(12) United States Patent
Shoemake et al.

(10) Patent No.: US 11,535,344 B2
(45) Date of Patent: Dec. 27, 2022

(54) SYSTEMS AND METHODS FOR THE MEASUREMENT OF CONTAMINANTS IN WATER

(71) Applicants: James M. Shoemake, Norman, OK (US); Michael Rainone, Palestine, TX (US); Samuel A. Sackett, Frankston, TX (US); Jonathan Jordan, Edmond, OK (US)

(72) Inventors: James M. Shoemake, Norman, OK (US); Michael Rainone, Palestine, TX (US); Samuel A. Sackett, Frankston, TX (US); Jonathan Jordan, Edmond, OK (US)

( * ) Notice: Subject to any disclaimer, the term of this patent is extended or adjusted under 35 U.S.C. 154(b) by 664 days.

(21) Appl. No.: 16/540,360

(22) Filed: Aug. 14, 2019

(65) Prior Publication Data

US 2020/0055577 A1  Feb. 20, 2020

Related U.S. Application Data

(60) Provisional application No. 62/718,388, filed on Aug. 14, 2018.

(51) Int. Cl.
| | |
|---|---|
| *B63B 32/70* | (2020.01) |
| *B63B 35/38* | (2006.01) |
| *G01N 33/00* | (2006.01) |
| *B63B 35/00* | (2020.01) |
| *B63B 22/18* | (2006.01) |

(52) U.S. Cl.
CPC .............. *B63B 32/70* (2020.02); *B63B 35/38* (2013.01); *G01N 33/0036* (2013.01); *B63B 22/18* (2013.01); *B63B 2035/007* (2013.01)

(58) Field of Classification Search
CPC ......... B63B 32/70; B63B 35/00; B63B 35/38; B63B 2035/007; G01N 33/0036
USPC .......................................................... 701/21
See application file for complete search history.

(56) References Cited

U.S. PATENT DOCUMENTS

| | | | |
|---|---|---|---|
| 4,293,225 A | 10/1981 | Wheaton et al. | |
| 4,394,573 A | 7/1983 | Correa et al. | |
| 5,974,860 A | 11/1999 | Kuroda et al. | |
| 6,269,763 B1 | 8/2001 | Woodland | |
| 7,470,917 B1 | 12/2008 | Hoang et al. | |
| 2010/0005857 A1* | 1/2010 | Zhang | G01C 13/00 73/29.02 |

(Continued)

FOREIGN PATENT DOCUMENTS

| | | | |
|---|---|---|---|
| CA | 3007379 A1 * | 12/2019 | ............. G01N 21/64 |
| JP | 2004028814 | 1/2004 | |

OTHER PUBLICATIONS

Mayerfeld "Fluorometers: Integration Experiences with Unmanned Vehicles" Turner Designs, 2017.

(Continued)

*Primary Examiner* — Lars A Olson
(74) *Attorney, Agent, or Firm* — Womble Bond Dickinson (US) LLP; Mark R. DeLuca

(57) ABSTRACT

The invention generally relates to the measurement and predictions of conditions and contaminants; chemical, particulate and gaseous in and around water impoundments. More specifically, the invention relates to the use of an autonomous watercraft to analyze the chemical and physical properties of a body of water, such as a pond holding water used in a hydraulic fracturing operation.

12 Claims, 7 Drawing Sheets

(56) References Cited

U.S. PATENT DOCUMENTS

2011/0004367 A1    1/2011   Saunders et al.

OTHER PUBLICATIONS

Malkov et al. "Oil-in-Water Fluorescence Sensor in Wastewater and Other Industrial Applications" (2010) Power Plant Chemistry 12(3), 144-154.
Pärt et al. "In-SItu Oil Detection Sensor—Technology Overview and Experiment Design" Technical Report for GRACE Grant No. 679266, published Oct. 31, 2016.

* cited by examiner

SYSTEMS AND METHODS FOR THE MEASUREMENT OF CONTAMINANTS IN WATER

PRIORITY CLAIM

This patent application claims priority to U.S. Provisional Application 62/718,388 filed Aug. 14, 2018.

BACKGROUND OF THE INVENTION

1. Field of the Invention

The invention generally relates to the measurement and predictions of conditions and contaminants; chemical, particulate and gaseous in and around water impoundments.

2. Description of the Relevant Art

The process of hydraulic fracturing (also known as "fracking") of a subsurface oil reservoir or fracking requires large quantities of water of a known content. The fracking is used to open fissures in the oil-bearing formation, but an assortment of other materials are injected under high pressure with the water including sand or other materials to hold the fractures open, these are called proppants. Also injected are materials to keep the sand suspended in the water such as guar gum, a plant-based polysaccharide, and a host of other chemicals such as bactericide, algaecides and pH balancing chemicals. However, the effectiveness of these chemicals depends on what is in the frack water before they are added to it. For instance, the acidity of the water influences the effectiveness of the polymerization of the suspension agent such as guar gum, which keeps the proppants in suspension. Similarly, knowing the pH will allow certain other chemicals to be added to correct the pH, thus improving the effectiveness of the suspension agent in keeping the proppant in suspension. In addition, the salinity of the water has an influence on the suspension as well. Thus, knowing the pH, salinity, the temperature as well as the suspended hydrocarbon content of the water prior to the addition of the fracking chemicals is important to the success of the frack job.

Most often a pond or surface reservoir is built to hold the water to be used on a frack job. On average, a frack job requires 5 million gallons of water. So a pond large enough to hold 5,000,000 gallons of water would be roughly 300'×200'×10' deep. A pond of this size would pose a significant challenge to a single point analysis of the water content. Even sampling around the edges of such a reservoir would introduce potential sampling errors by only taking samples from the edges of the pond. Understanding the nature of the constructed frack pond shows why such methods are ineffective. Each pond or surface reservoir is created with sloped sides and then lined with a plastic liner. Sampling from the sides around the pond is inaccurate because of the side and the shallow samples taken from the edge of such a pond may not be representative of the water in the center of the pond at a 10' depth. The embodiments described herein address this problem.

It is known that the water composition of the water in a frack pond can change under various atmospheric conditions. Rain can dilute the pH, decrease the salinity; high winds and the level of solar insolation can reduce the volume of water through evaporation, thus changing pH and salinity. Sunlight will increase algae and bacterial growth, which increases the toxin load, including hydrogen sulfide, making off-gassing of the pond dangerous and water unfit for either fracking or discharge.

In addition, a frack pond is created by the dumping various water sources into it, such as from a lake, stream, water well or from flow back water from a frack job or even producing well flow back water after being cleaned, each load potentially changing the composition. It cannot be assumed that the composition of the pond at the shallow edge of the pond is the same as in any other part because of the uncertainty of the source of added water as well as the uncertainty of mixing agents such as the wind and point source additions.

When a well is to be fracked, the operator will sample the water in the pond to determine what chemicals are required to prepare the water to receive the fracking chemicals. This sampling process is most often done by hand by a technician that removes the water from the pond to test in a lab. The results, which most often take from 1 to 3 weeks, are reported to the operator who then contracts a chemical company to mix additive to the water to prepare it to take the fracking chemicals and proppant load.

Another serious drawback to the current process, in addition to the location and limitation of the sampling, is the time it takes to sample and then analyze the current condition of the frack pond. During the period between the sample being taken and the results being reported back to the operator, the condition of the water could change thus making the chemical intervention invalid. In addition, heavy materials in the water as well as salt concentration stratify such that a reading a one depth may not be reprehensive of the concentration at another.

SUMMARY OF THE INVENTION

In an embodiment, an autonomous watercraft for analyzing a body of water used for hydraulic fracturing includes:
  a hull that supports the autonomous watercraft in water such that the autonomous watercraft floats on the surface of the body of water;
  a propulsion system coupled to the hull. The propulsion system propels and directs the autonomous watercraft in the body of water;
  a water sensor system which includes one or more water sensors submersible in the body of water. One or more of the water sensors are capable of determining the presence of hydrocarbons and/or sulfides in the body of water.
  a deployment system capable of deploying the water sensor system into the body of water. The deployment system can vary the depth of the water sensor system in the body of water;
  an air sensor system that includes one or more air sensors for detecting volatile organic compounds and/or toxic inorganic gases in the air surrounding the autonomous watercraft;
  a wireless communication system; and
  a processor operably coupled to the deployment system, the propulsion system, and the wireless communication system. The processor is configured to execute non-transitory program instructions. The program instructions are operable to:
    automatically deploy the water sensor system into the water at a predetermined depth and a predetermined location;
    automatically operate the air sensor system;

automatically propel the autonomous watercraft to a different location from the predetermined location in the body of water; and automatically collect data from the water sensor system and/or the air sensor system and transmit the collected data to a location remote from the autonomous watercraft.

In some embodiments, the hull includes one or more pontoons, wherein at least one of the one or more pontoons comprises at least one compartment.

In some embodiments, the water sensor system includes one or more water sensors such as pH sensors, salinity sensors, temperature sensors, turbidity sensors, and water depth sensors. The water sensor system may include a water sensor module, the water sensor module comprising a body, a channel running through the body, UV and/or visible light sources, and fluorescence and/or absorption detectors. The water sensor module may be coupled to the hull by a cable such that, during use, the sensor module is pulled through the water, under the hull.

In some embodiments, the air sensor system comprises one or more air sensors such as temperature sensors, barometric pressure sensors, and humidity sensors. In an embodiment, an air sensor detects toxic inorganic gases in the air surrounding the autonomous watercraft. The air sensor may detect the presence of hydrogen sulfide.

In some embodiments, the deployment system comprises at least one cable coupled to a motor.

In one embodiment, the processor is operable to provide commands to automatically propel the watercraft along a predetermined route within the body of water. The processor may also be operable to alter the predetermined route based on instructions received via the wireless communication system.

In an embodiment, a system for analyzing a body of water used for hydraulic fracturing includes an autonomous watercraft, as described herein, and a weather station either positioned in the vicinity of the body of water or built into the watercraft. The weather station measures one or more environmental conditions such as temperature, humidity, rainfall, wind speed wind direction, and solar radiation. During use, the autonomous watercraft may be operated to analyze the body of water when a change in the environmental conditions is detected by the weather station.

In an embodiment, a method of analyzing a body of water used for hydraulic fracturing includes:

placing an autonomous watercraft, as described herein, in the body of water. The autonomous watercraft is programmed to:

automatically measure and map the depth of the body of water automatically deploy the water sensor system into the water at a predetermined depth and a predetermined location;

automatically operate the air sensor system;

automatically propel the autonomous watercraft to a different location from the predetermined location in the body of water; and automatically collect data from the water sensor system and/or the air sensor system and transmit the collected data to a location remote from the autonomous watercraft.

In some embodiments, the autonomous watercraft moves along a predetermined route within the body of water. In some embodiments, the method includes altering the predetermined route based on data obtained from the water sensor system. The predetermined route may be altered such that the autonomous watercraft is directed to chemically non-homogenous regions of the body of water.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
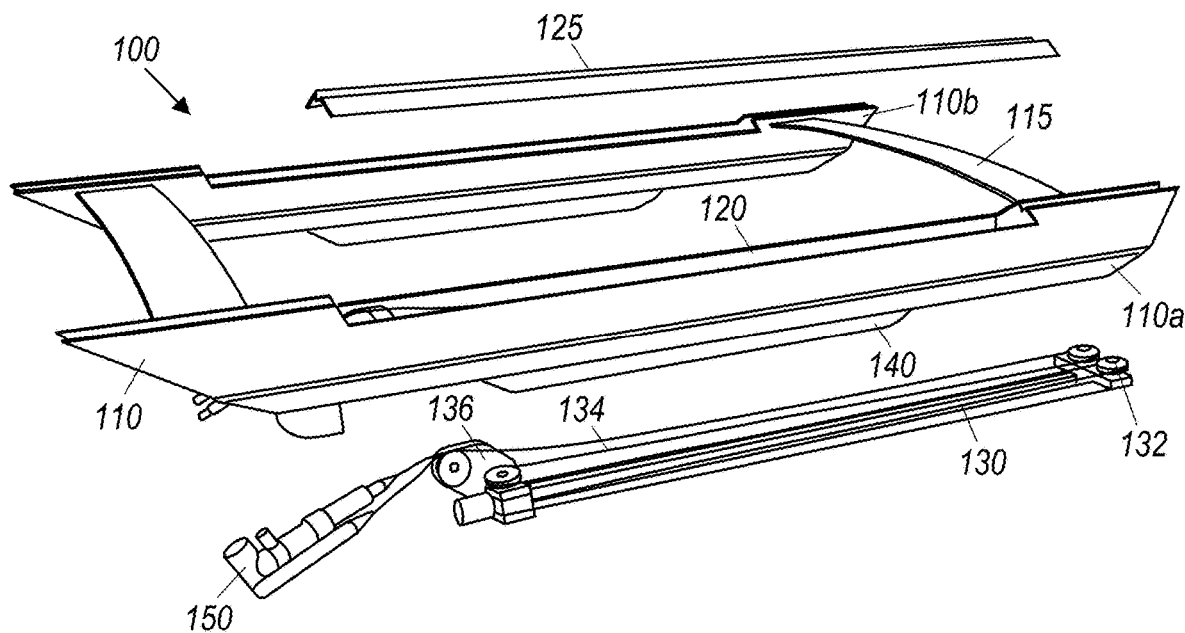
FIG. 1A depicts an exploded view of an autonomous watercraft.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

In an embodiment, a smart, predictive system may be used to monitor the water quality and/or the air quality, in a body of water used for hydraulic fracturing. The system is embodied as an autonomous watercraft that uses a suite of water and air sensors for measuring important contaminants in the water and the air. The system may also include sensor for determining environmental conditions in the atmosphere that could influence the quality of the water and then predict future changes to that water given the environmental current and future environmental conditions. The air sensors would be present to detect gaseous emissions produced in the water from the chemical contaminants associated with the hydraulic fracturing process. In this case, dangerous emissions, such as hydrogen sulfide could be avoided and proper measures could be taken to avoid fatalities. Once all of the conditions are understood, the customer would be able to add chemicals in appropriate quantities to prepare the water for the fracking.

Thus, in one embodiment an autonomous watercraft includes a hull configured to support the autonomous watercraft in water such that the autonomous watercraft floats on the surface of the body of water. The autonomous watercraft also includes a propulsion system coupled to the hull, wherein the propulsion system is configured to propel and direct the autonomous water craft in the body of water. The apparatus could be self-powered or moved by wire or pushed, guided or unguided, in a random or planned pattern to sample the water and air above the water. In an embodiment the aquatic apparatus could float or could be submerged in an underwater vehicle. In another embodiment said apparatus could be moved by an aerial drone, which would lift the sensor suite from one position to another. Said drone could then, move the sensor suite from one impoundment to another to repeat said measurement activity. In some embodiments the apparatus could be remotely piloted from the shore, or from a remote location using video, or could be programmed using autonomous software to guide itself to each sampling location, including movement from impoundment to impoundment.

The autonomous watercraft also includes a water sensor system comprising one or more water sensors submersible in the body of water, wherein one or more of the sensors are capable of determining the presence of hydrocarbons and/or sulfides in the body of water used during hydraulic fracturing. The water sensor system may further include, but not be limited to: pH sensors, salinity sensors, temperature sensors, turbidity sensors, and water depth sensors.

In one embodiment, the water sensor system may be lowered into the body of water to differing depths to detect concentration changes that may occur by settling, temperature based thermosiphoning, or wind mixing. In one embodiment, the autonomous watercraft includes a deployment system capable of deploying the water sensor system into the body of water, wherein the deployment system is configured to vary the depth of the water sensor system in the body of water. In an embodiment, the water sensor is coupled to a winch system which can raise or lower the water sensor with respect to the surface of the body of water.

In an embodiment, the autonomous watercraft includes air sensor system comprising one or more air sensors for detecting volatile organic compounds and/or toxic inorganic gases in the air surrounding the autonomous water craft. The air sensor system, in addition, may also include, but is not limited to temperature sensors, barometric pressure sensors, and humidity sensors.

In one embodiment, a weather station could be placed either on the watercraft or proximate to the body of water to detect microclimatic changes that may impact contaminant changes. Rainfall, solar insolation, temperature, relative humidity, wind direction and velocity and barometric pressure could be monitored as factors that could change pond conditions. In one embodiment, the weather station could receive weather data from the NOAA website using typical communication techniques such as the cell network or via the internet that would allow the microclimatic conditions at the impoundment to be coordinated with the measurements of the sensor, for more accurate sensing of contaminant levels.

In one embodiment, the water borne sensors, the air sensors and the weather sensors would all communicate with a remote station via cell, satellite, internet such the data from the sensors and the weather station could be remotely monitored, cataloged, filtered and be otherwise readied for interpretation by either persons expert in the art of interpretation such that when the client is ready a proper mix of chemicals can be made ready for mixing into the water in preparation for the fracking job.

In one embodiment, autonomous watercraft could be carried by an unmanned aerial vehicle (UAV) which could land the autonomous watercraft on the water at various locations for sampling, and/or could include a sensor package that could be lowered to various depths by the hovering vehicle. In another embodiment, the UAV could carry the water sensor system and the air sensor system. The UAV could then land on the water and then, using a form of hoist, lower the water sensor package to various depths for proper sampling.

In one embodiment, the UAV might have a home base near a group of impoundments that would allow for deployment, recovery, recharging and maintenance of the UAVs. Such a home base might be a truck, trailer or other method of housing the UAVs that might include a communication system to act as a relay for the data gathered, might be housing for a human operator that might include video monitor and control of multiple UAVs over a multiple of ponds.

In one embodiment, an autonomous watercraft system for taking real time measurements of the chemical contents of frac water and industrial water ponds, including the surrounding environments that might affect such ponds over time is used to allow operators and owners virtually immediate access to properly treated water.

In an embodiment, the system is used to ensure that the water quality in a frac pond or reservoir is maintained at the predetermined specification. The method of maintaining the pond at the proper chemical content includes a measurement step, a data aggregation step, a data analysis step, and an intervention step.

The measurement of the critical parameters of the pond will be taken autonomously, via a floating device that navigates the pond in a programmed manner. In another embodiment the path of sensing could change according to the learning of the device and areas of significant differences could be more intensely monitors. At the same time, atmospheric measurements of pond environment will be measured to understand the dynamic changes that the pond is undergoing by evaporation, rainfall and purposeful addition.

The data from the in-water and above water sensors as well as the weather station will be aggregated and parsed to ensure that actionable data is sent to the lab personnel.

The data will be relayed to the lab via the internet so that the real time conditions of the pond can be analyzed and an intervention plan can be prepared and the updated as pond conditions evolved.

When time for pond use is at hand, the constantly updated condition of the pond will provide the information required to allow for an appropriate chemical intervention of the pond for use.

The primary vehicle for data gathering includes one or more thrusters, which are autonomously controlled. The hull may be a pontoon type hull (e.g., a double pontoon hull) that will carry all of the instrumentation in a water-resistant environment. The hull includes a deployment system for raising/lowering the water sensors to the proper depth for measurement. Electronics, batteries and autopilot for the autonomous watercraft will be carried in a water-resistant container in the hull.

Figure 1B:
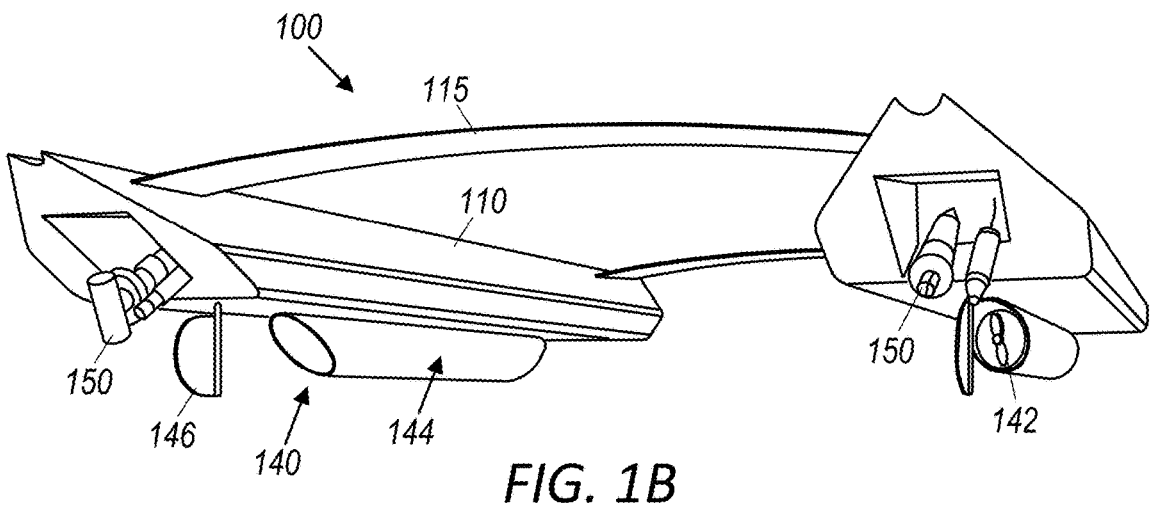
FIG. 1B depicts a perspective view from the bottom side of the autonomous watercraft.

An exemplary single hull watercraft system is described in U.S. Patent Application Publication No. 2011/0004367 to Saunders et al., which is incorporated herein by reference. A watercraft system using dual pontoons as the hull is shown in FIGS. 1A and 1B. Watercraft 100 includes pontoons 110 which provide the necessary buoyancy to maintain the watercraft on the surface of the water. In the embodiment depicted in FIGS. 1A and 1B, the watercraft includes two pontoons, 110a and 110b, however it should be understood the watercraft may include more than two pontoons in other embodiments. Pontoons 110 are coupled together by one or more support members 115 as shown in FIG. 1. One or more of the pontoons may include a compartment 120 which may be used to hold the various electronic components, power supplies, solar cells for recharging the batteries, motors used to operate the watercraft and sensors. Compartment 120 includes a cover 125 and other components (e.g., seals, gaskets, etc.) that make the compartment substantially waterproof.

Figure 2A:
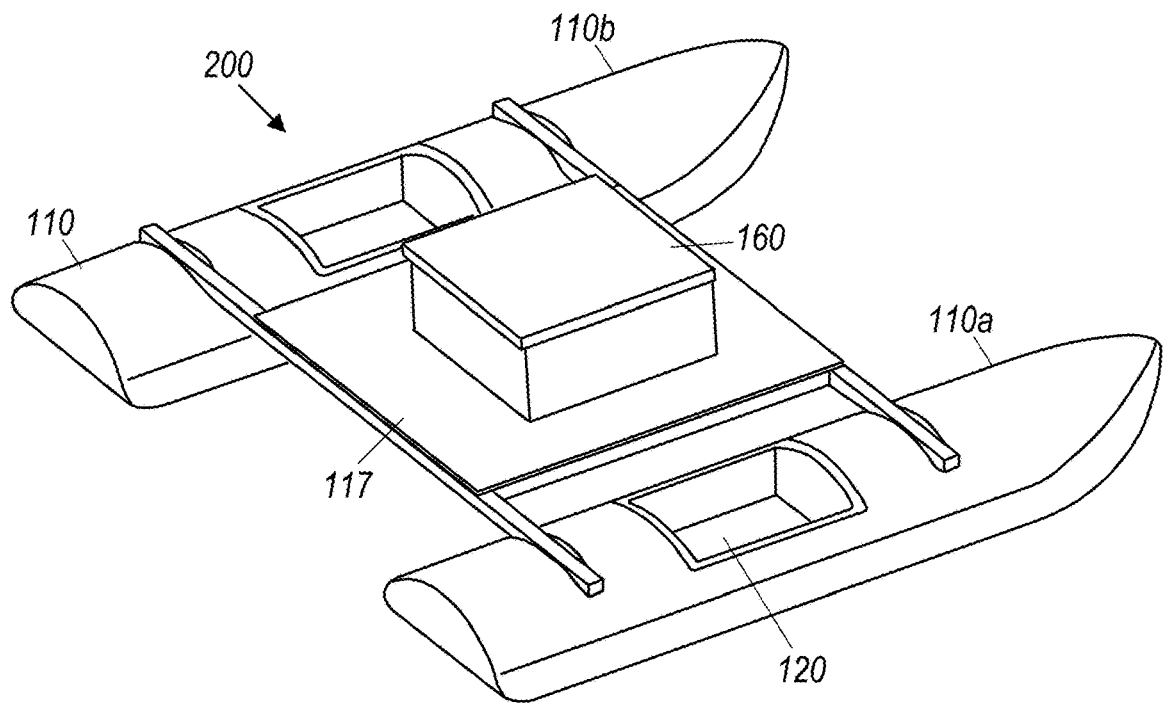
FIG. 2A depicts a perspective view of an alternate embodiment of the hull of an autonomous watercraft.
Figure 2B:
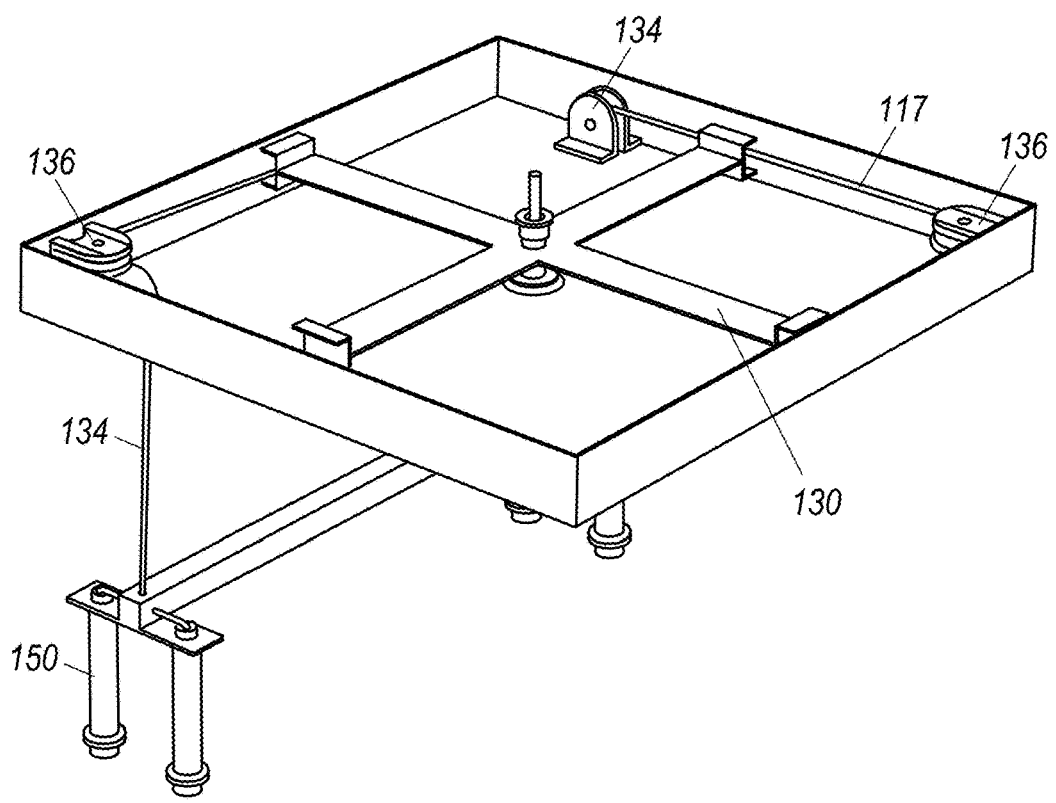
FIG. 2B depicts a perspective view of the bottom of the deployment system of the alternate embodiment of the hull of an autonomous watercraft.

FIGS. 2A and 2B depict an alternate embodiment of a watercraft 200 having dual pontoons 110 as a hull. In this embodiment, the watercraft includes dual pontoons 110a and 110b and compartments 120, as described above for the embodiment depicted in FIG. 1. In contrast to the embodiment of FIG. 1, the watercraft includes a platform 117, which couples pontoons 110 together to form the hull of the watercraft.

The watercraft 100 includes a propulsion system 140 coupled to pontoon 110, most easily seen in FIG. 1B. The propulsion system is configured to propel and direct the watercraft in the body of water. The propulsion system may include one or more propellers 142 coupled to a motor (not shown) that is disposed in the pontoon body 110. Propellers 142 may be disposed inside a propulsion tube 144 which guides water toward propeller. One or more filters (not shown) may be placed at the inlet of the propulsion tube to filter out debris and other particulate matter that may impair the operation of the propellers. Propulsion system 140 also includes one or more rudders 146 to guide the watercraft over the body of water.

The watercraft 100 also includes a deployment system 130 capable of deploying a water sensor system 150 into the body of water. The deployment system is configured to vary the depth of water sensor system 150 in the body of water. Deployment system 130 includes a series of pulleys 132 through which a cable 134 is pulled to deploy the water sensor system. A two directional motor 136 is used to collect or release the cable, allowing the water sensor system to move toward or away from the watercraft, respectively. Deployment system 130 may be disposed in a non-sealed portion of a pontoon 110, as shown in FIG. 1B. In some embodiments, multiple water sensors may be coupled to different deployment systems and disposed in different portions of the watercraft.

In an alternate embodiment, the deployment system may be incorporated into a platform (for example, platform 117 in the embodiment depicted in FIG. 2). As depicted in FIG. 2B a deployment system 130 is incorporated into the platform 117. A water sensor system 150 is attached to platform 117 by cables 134 extending from platform 117. Each of the cables 134 are attached to individual motors 136 via pullies 132. During use each motor 136 may be independently operated to raise, lower, or angle the water sensor system.

A processor is operably coupled to the deployment system and the propulsion system, the processor configured to execute non-transitory program instructions. The processor is positioned within one of the watertight compartments of the watercraft. The processor will perform a number of functions that enable the watercraft to operate autonomously in a body of water. The processor is configured to provide signals to perform various operations associated with movement of the vehicle. For example, the processor may provide control signals to the propulsion system with instructions to propel and steer the watercraft to a new location. The processor may also be configured to operate the deployment system to deploy the water sensor system into the water at a predetermined depth and at predetermined times. The processor may also be configured to operate an air sensor system. The processor may also automatically collect and transmit data collected from the water sensor system and/or the air sensor system to a location remote from the autonomous watercraft.

Figure 4:
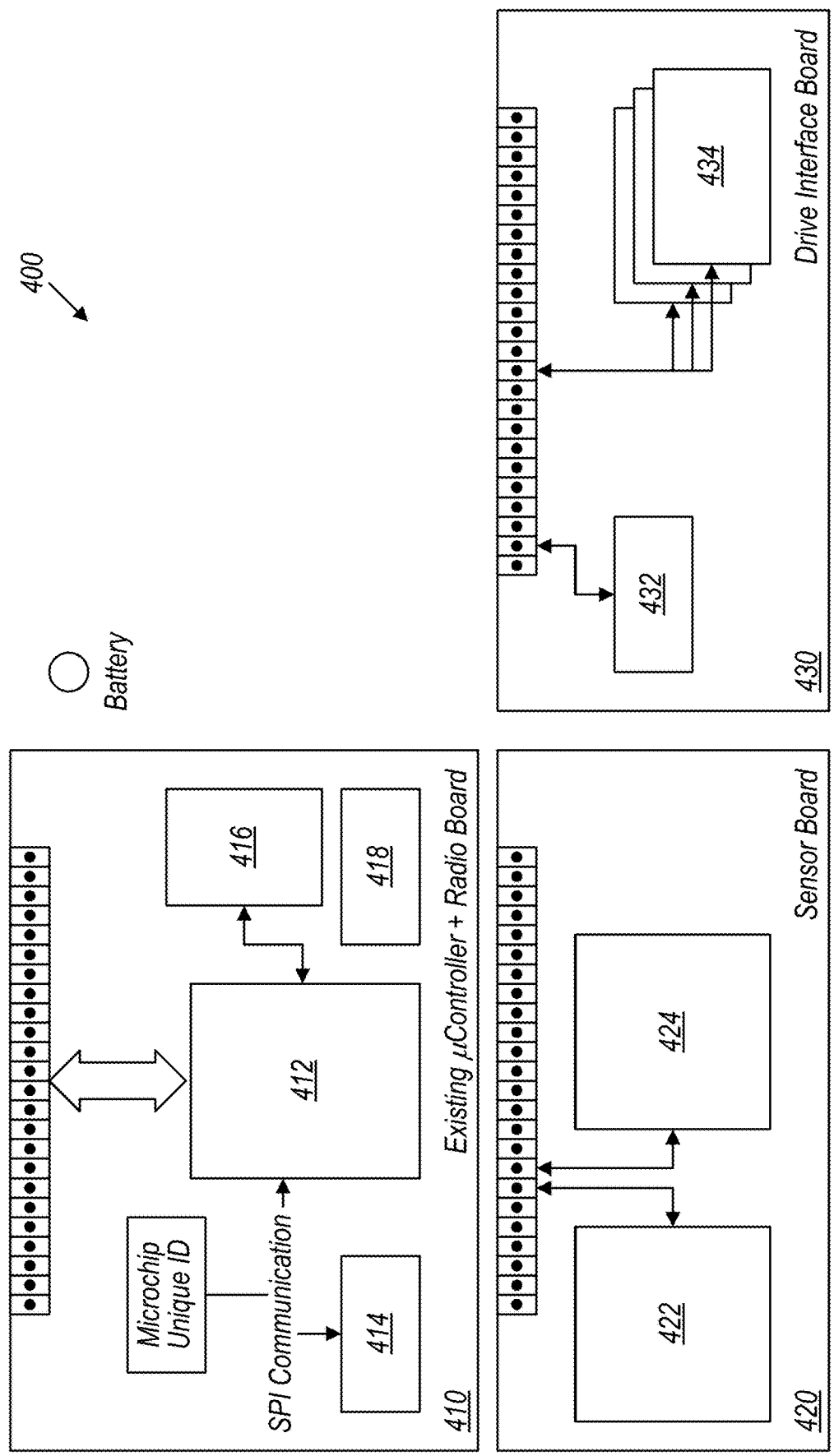
FIG. 4 depicts a schematic diagram of an electronics system for an autonomous watercraft.

FIG. 4 depicts a schematic diagram of a control system 400 for an autonomous watercraft. Control system 400, in one embodiment, is composed of a control board 410, a sensor board 420, and a driver interface board 430. Control board 410 includes a processor 412, memory 414, and a communication system 416. A DC-DC convertor 418 may also be coupled to the electronic components. Control board is coupled to sensor board 420. Sensor board 420 couples sensors from the water sensor system 422 and the air sensor system 424 to the processor. Drive interface board 430 includes an operation controller 432 that controls the operation of the propulsion system and the deployment system. Operation controller 432 interfaces with the various components of the propulsion system and the deployment system through various relays 434 which switch the various components on or off.

Figure 3:
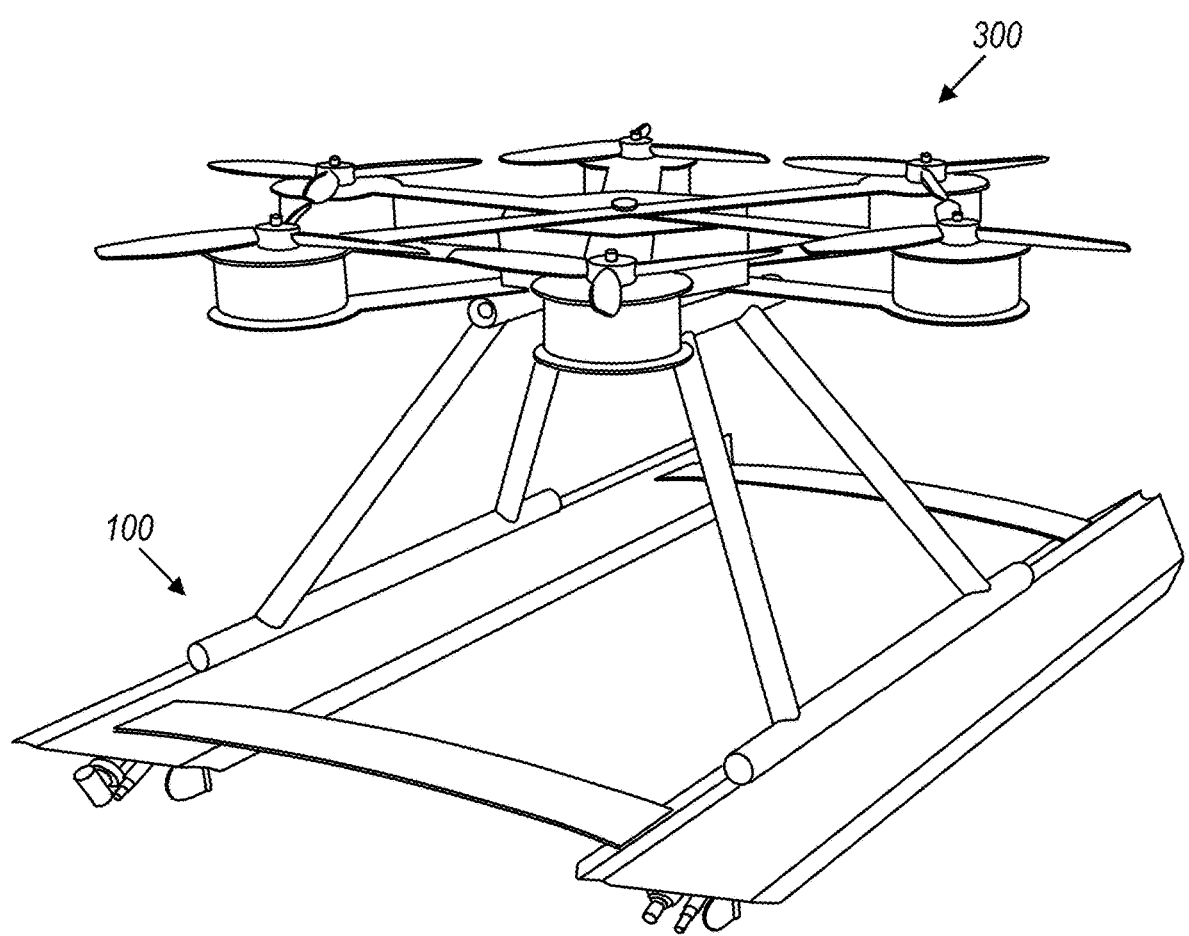
FIG. 3 depicts a perspective view of an autonomous watercraft coupled to an unmanned aerial vehicle.

The hull, in some embodiments, is designed to be mated to an unmanned aerial vehicle ("UAV") to allow movement of the watercraft from one pond to another. FIG. 3 depicts a UAV 300 coupled to the pontoon design of the embodiment of FIG. 1. It should be understood that the embodiment of FIG. 2 may also be similarly coupled to a UAV. The pontoon design offers an advantage over other designs when coupled to a UAV. The pontoon design presents a low wind profile making it aerodynamically efficient during aerial transport. In a typical embodiment, the expected total weight of a watercraft/pontoon/UAV is approximately 25 lbs., with the watercraft (with sensors, electronics, batteries, weighting about 14 lbs. and the UAV weighing about 11 lbs. A hexacopter (or other multiple blade UAV) was chosen for the following reasons: (a) better lifting capability, (b) more reliable, can fly on 4 functioning motors, and (c) more capable for special tilting maneuver.

As noted previously, the electronics components of the system may include a communication system 416. The communication system may include Wi-Fi, a cellular modem, Bluetooth and/or a 915 MHz radio. The communication system, in some embodiments, includes a 915 MHz transceiver, a Wi-Fi module, a Bluetooth module and a cell phone connection. Use of such a communication system offers the advantages of no measurements directly into the communication system, only over radio link. Weather measurements are sent to the communication system over a serial link (DART). On-board measurements are sent to the communication system over the air.

The autonomous watercraft is designed, in some embodiments, to provide analytical data from multiple samples obtained from a body of water. When used to analyze water used in a fracking process, the autonomous watercraft includes a water sensor system comprising one or more water sensors submersible in the body of water. In some embodiments, one or more of the sensors can determine the presence of hydrocarbons and/or sulfides in the body of water used during hydraulic fracturing. The water sensor system may further include, but not be limited to pH sensors, salinity sensors (conductivity sensors), temperature sensors, turbidity sensors, and water depth sensors. A summary of sensors that may be present in the water sensor system are set forth in Table 1.

TABLE 1

| Measured Quantity | Range | Measurement Frequency | Usage | Manufacturer | Part No. |
|---|---|---|---|---|---|
| Conductivity | 5-200,000 µS/cm | 30 sec | Salinity | Atlas | IECK 1.0 |
| pH | 0-14 | | | Atlas | IpH |
| $H_2S$ | 50 µg/l-10 mg/l 500 µg/l-50 mg/l | | Sulfates | AMT | |
| Depth | 0-15 ft. | | Sensor Depth | MaxBotix | D10D |
| Temperature | −200-850° C. | | | Atlas | PT-1000 |

Figure 5:
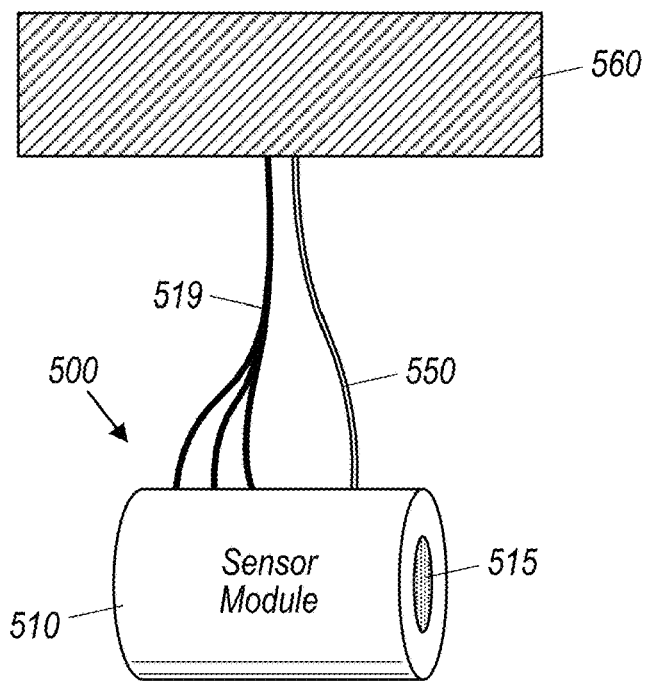
FIG. 5 depicts a side view of a water sensor module.
Figure 6:
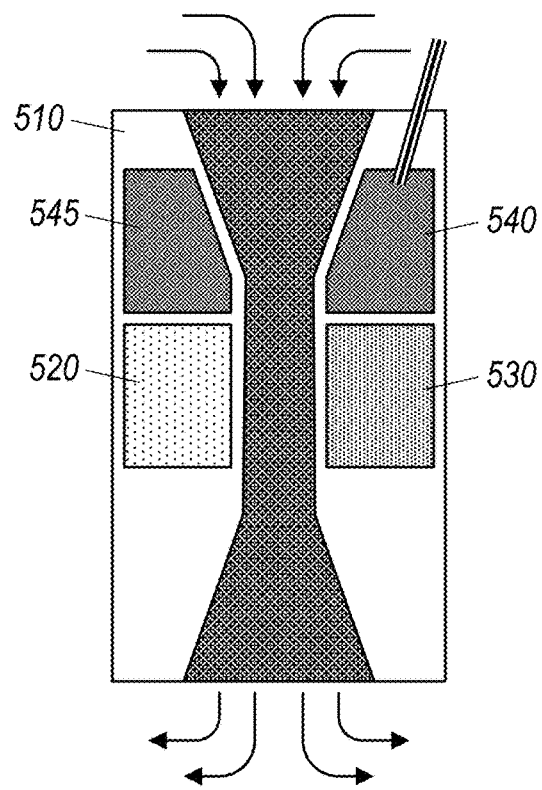
FIG. 6 depicts a section view of a water sensor module.

To enable onboard water sensors to quickly and accurately determine the various physical and chemical properties of the body of water, a water collection and analysis device is used. FIG. 5 depicts a side view of a water sensor module 500. FIG. 6 depicts a schematic diagram of the internal components of water sensor module 500. In the depicted embodiment, sensor module 500 includes a body 510 having a channel 515 running through the body. As shown in FIG. 6, the channel allow water to flow into and through body 510. Disposed in the body are UV and/or visible light sources 520 which can be used for spectrophotometric analysis. As the water passes through sensor body 510, light from light sources 520 are passed through the water sample. After passing through the water, the light as collected by fluorescence and/or absorption detectors 530. The data collected from detectors 530 is collected and analyzed by on-board data processing components 540 and associated electronics 545. Sensor module 500 is coupled to the watercraft by a cable 550, for example, or other type of connector. One or more power cables and/or one or more data cables 519 are also coupled to the water sensor module to provide power and transfer information about the body of water to a remote site. The water sensor module is typically suspended under the watercraft 560 during use. In some embodiments, the water sensor module is coupled to the hull by a cable such that, during use, the sensor module is pulled through the water, under the hull.

There is a need in the petroleum industry to measure the concentration of emulsified suspended crude oil in water collected at hydraulic fracturing facilities. A specialized hydrocarbon sensor is capable of measuring suspended oil at concentrations below 5%. A sensor module, such as sensor module 500, measures the fluorescent visible light from the oil particles stimulated by an ultraviolet light emitting diode (LED) at a wavelength of 465 nm. Optical detectors measure the intensity of this light, which is proportional to the concentration of oil particles in the oil/water mixture.

A technical difficulty arises when the density of oil particles becomes great enough to absorb some of the fluorescent light before it reached the optical detector, thereby creating incorrect measurement of the fluorescent light intensity. A method was devised to compensate for this effect in which a simultaneous measurement of visible light transmitted through the oil/water sample is used to mathematically correct for the decreased fluorescent light measurement.

Optical detector(s) measures both the fluorescent light, F, and the visible transmitted light, T. Both measured values are normalized to a value of 100% at the highest reading recorded. The normalized fluorescent data is then divided by the normalized transmission data to yield the corrected value of fluorescent intensity which is independent of the absorption by oil particles.

Figure 7:
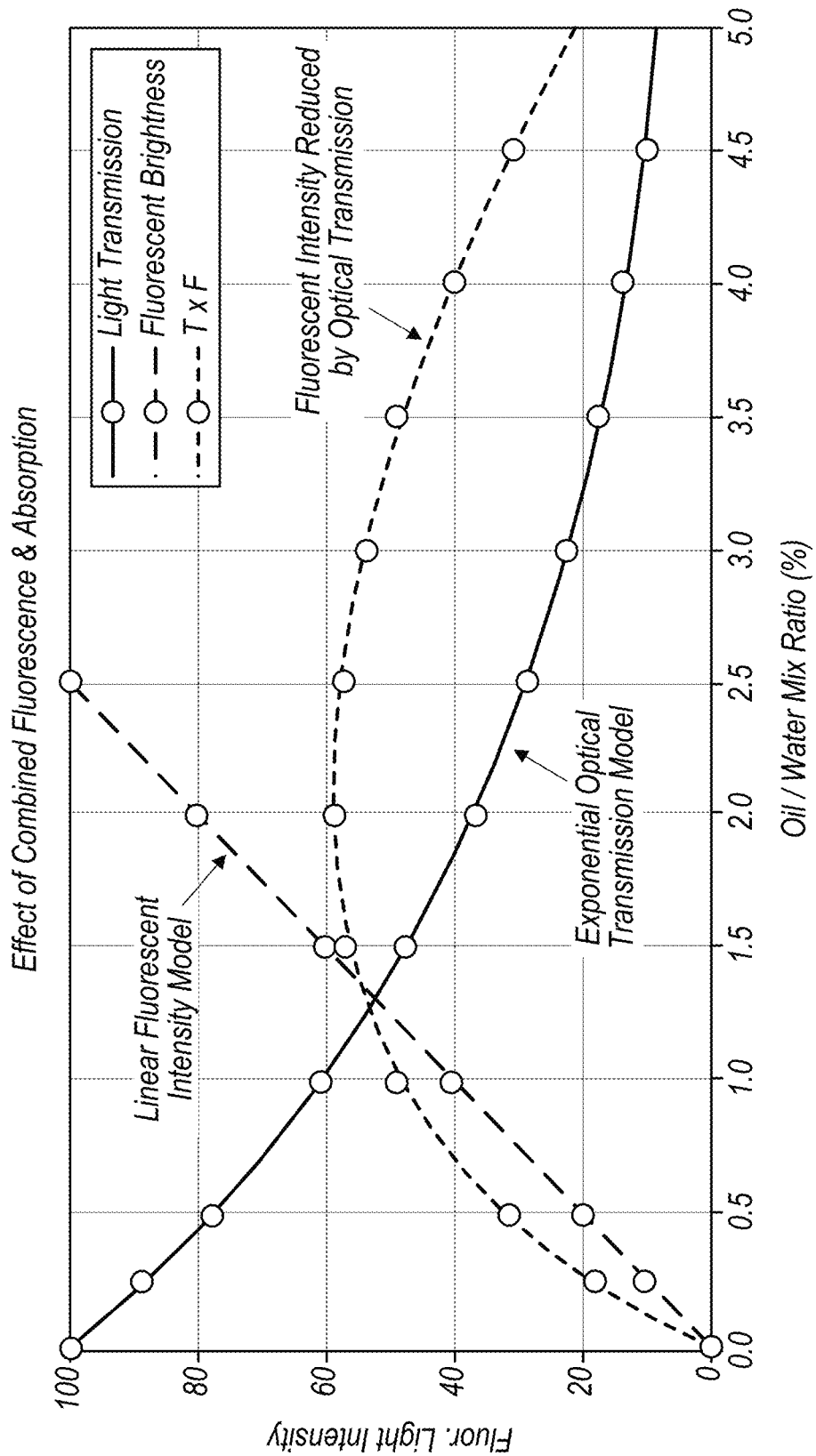
FIG. 7 depicts a graph of fluorescent light intensity vs. oil/water ratio.

FIG. 7 depicts a graph of fluorescence uncorrected (T×F) which shows a non-linear change in the fluorescence light intensity as the oil/water ratio increases. If normalization is used, a linear relationship between the fluorescent light intensity and the oil/water ratio increases, allowing more accurate determination of the concentration of hydrocarbons in the sample of water.

In an embodiment, the autonomous watercraft includes air sensor system comprising one or more air sensors for detecting volatile organic compounds and/or toxic inorganic gases in the air surrounding the autonomous watercraft. Toxic inorganic gases include but are not limited to carbon monoxide (CO), bromine ($Br_2$), nitrogen dioxide ($NO_2$), hydrogen ($H_2$), sulfur dioxide ($SO_2$), ozone ($O_3$), hydrogen cyanide (HCN), fluorine ($F_2$), chlorine dioxide ($ClO_2$), hydrogen sulfide ($H_2S$) and Chlorine ($Cl_2$). Sulfides include hydrogen sulfide, hydrogen sulfide salts and metal sulfide salts. The air sensor system, in addition, may also include, but is not limited to temperature sensors, barometric pressure sensors, and humidity sensors. Table 2 lists some of the most common air sensors that may be used.

TABLE 2

| Measured Quantity | Range | Measurement Frequency | Usage | Manufacturer | Part No. |
|---|---|---|---|---|---|
| Temperature | −40 to 185° F. | 30 sec | | | |
| Humidity | 0-100% | | | Atlas | IpH |
| Pressure | 300-1100 mBar | | | Bosch | BME680 |
| VOCs | | | | Analox | ACG+ |
| TIG | | | | Analox | MEC |

A home base is set up in the vicinity of the fracking operations to allow local control and acquisition of data from the autonomous watercraft. The home base is the centralized center for communication from each pond communication system. The home base is also the maintenance and charging center for the watercraft. The home base may also be lodging for operators during work shifts. Home base may also house a server base for data analytics prior to sending to internet. The home base may also include equipment to allow FPV control to allow operator to oversee watercraft movement from pond to pond.

At the home base (or any other location in the vicinity of the fracking operation, including on the watercraft), a weather station may be established to monitor environmental conditions. Exemplary components of a local weather station are presented in Table 3. In some embodiments, the autonomous watercraft is operated to analyze the body of water when a change in the environmental conditions is detected by the weather station.

TABLE 3

| Measured Quantity | Range | Measurement Frequency | Usage | Manufacturer | Part No. |
|---|---|---|---|---|---|
| Temperature | −40 to 185° F. | 30 sec | | Acurite | 5 in 1 PRO Weather Station Model 06014RM |
| Humidity | 0-100% | | | | |
| Rainfall | Inches or mm | | | | |
| Wind Speed | 0-99 mph | | | | |
| Wind Direction | 16 points | | | | |
| Solar Radiation | 0-1280 W/m$^2$ | | | Onset | S-LIB-M003 |

Most fracking sites are in remote locations which will require set-up of the home base and infrastructure required to remotely collect samples and analyze the collected data. Prior to set up, the operator establishes the overall site operation and home base. If multiple ponds are to be analyzed, the operator establishes the location for a gateway and weather station if not on the watercraft, power if available, and communications links for the overall area operation. If Wi-Fi is available, establish connection, if not, set up cell network. If no power supply is present, a location for solar panels is established. After the infrastructure is established and operating the operator will begin creating a map of the fracking pond(s) for the particular chemical(s) or physical properties of interest.

Figure 8:
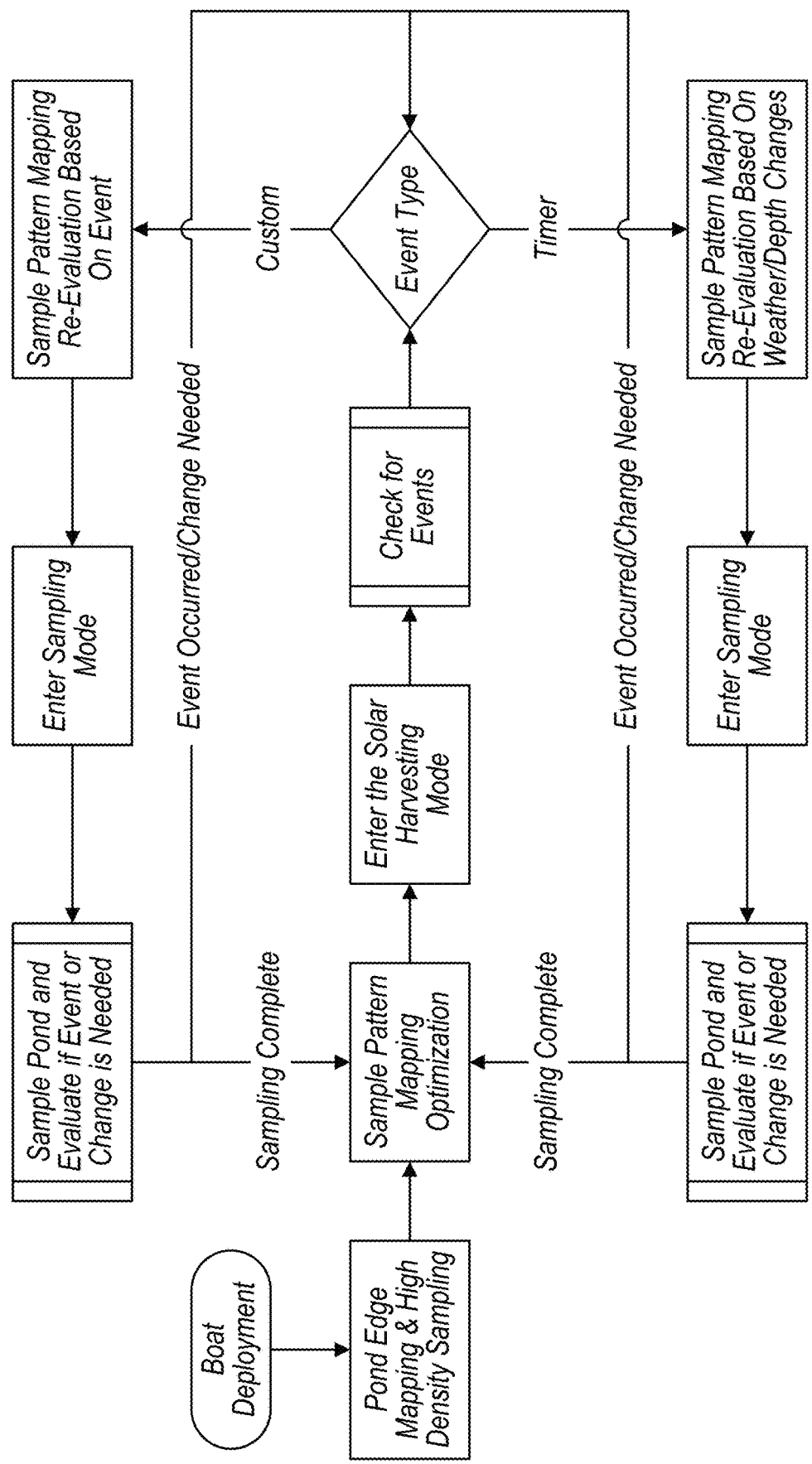
FIG. 8 depicts a flow chart of a method of sampling a body of water with an autonomous watercraft.

FIG. 8 depicts a flow chart showing the process of mapping a body of water associated with a fracking operation. To create such a map, the operator will place the watercraft in the pond (Boat Deployment). The watercraft drives the perimeter to establish an outline of the pond and stores the perimeter location as permanent parameter (Pond Edge Mapping). After establishing the perimeter, the first mapping is performed using high density sampling. High density sampling is performed by collecting water sample data at varies depths at each location where the watercraft stops. (High Density Sampling). After driving the initial route, the operator communicates with the home base to insure proper logging and data acquisition. This process is repeated for each pond in area. The operator returns to home base to establish route and timing of the optimal sampling pattern.

After the high-density sampling is complete, a detailed map of the fracking pond is analyzed and an optimized route is established (Sample Pattern Mapping Optimization). Sample pattern optimization is performed by analyzing the collected data and looking for chemically non-homogenous regions in the body of water. Chemically non-homogenous regions in the body of water are regions in which the water sensor system determines that one or more of the tested properties are greater than 10% of the average value of the property in the body of water. For example, if the average salt level in the body of water is 1%, a region having a salt content of 1.1% or greater would be considered a non-homogenous region. Once chemically non-homogenous regions are identified, the sampling pattern can be optimized by having the watercraft learn to focus, primarily, on the non-homogenous regions.

When not being used the watercraft may go into a position on the pond which will allow for maximum solar exposure to allow solar panels to recharge the batteries (Enter the Solar Harvesting Mode).

Numerous events can occur that will modify the composition of the pond (Check for Events). For example, weather conditions (rain or heavy winds) can cause significant changes to the chemical composition of the pond, due to redistribution, within the pond, of chemicals captured during the fracking process. Other events include fracking operations which withdraw or add water to the pond, and addition of chemicals to the pond to alter the chemical composition. If an event occurs, the type of event is identified, and the appropriate action is taken (Event Type). In the event of a Timer event (e.g., weather changes) or a Custom event (e.g., addition of chemicals to the frack pond) the pond is resampled and remapped. The new map is analyzed, and a new optimized sampling routine developed. This iterative process ensures that the pond is properly analyzed and an accurate determination of the state of the fracking pond can be made.

The combination of an autonomous watercraft comprising a plurality of sensors for determining the concentration of chemicals associated with fracking ponds, and the build up using Edge Computing of an optimized sampling routine leads to a more accurate determination of the chemical constitution of the fracking pond. This in turn, leads to the use of optimized and proper amounts of chemicals to prepare the water before additional fracking operations are initiated.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An autonomous watercraft for analyzing a body of water used for hydraulic fracturing comprising:
    a hull configured to support the autonomous watercraft in water such that the autonomous watercraft floats on the surface of the body of water;
    a propulsion system coupled to the hull, wherein the propulsion system is configured to propel and direct the autonomous watercraft in the body of water;
    a water sensor system comprising one or more water sensors submersible in the body of water, wherein one or more of the water sensors are capable of determining the presence of hydrocarbons and/or sulfides in the body of water;
    a deployment system capable of deploying the water sensor system into the body of water, wherein the deployment system is configured to vary the depth of the water sensor system in the body of water;
    an air sensor system comprising one or more air sensors for detecting volatile organic compounds and/or toxic inorganic gases in the air surrounding the autonomous watercraft;
    a wireless communication system; and
    a processor operably coupled to the deployment system, the propulsion system, and the wireless communication system, wherein the processor is configured to execute non-transitory program instructions, wherein the program instructions are operable to:
        automatically deploy the water sensor system into the water at a predetermined depth and a predetermined location;
        automatically operate the air sensor system;
        automatically propel the autonomous watercraft along a predetermined route within the body of water, wherein the processor is operable to alter the predetermined route based on learning of anomalous reading, and/or instructions received via the wireless communication system; and
        automatically collect data from the water sensor system and/or the air sensor system and transmit the collected data to a location remote from the autonomous watercraft.

2. The autonomous watercraft of claim 1, wherein the hull comprises one or more pontoons, wherein at least one of the one or more pontoons comprises at least one compartment.

3. The autonomous watercraft of claim 1, wherein the water sensor system comprises one or more water sensors selected from the group consisting of pH sensors, salinity sensors, temperature sensors, turbidity sensors, and water depth sensors.

4. The autonomous watercraft of claim 1, wherein the water sensor system comprises a water sensor module, the water sensor module comprising a body, a channel running through the body, UV and/or visible light sources, and fluorescence and/or absorption detectors.

5. The autonomous watercraft of claim 4, wherein the water sensor module is coupled to the hull by a cable such that, during use, the sensor module is pulled through the water, under the hull, the watercraft stops at a predetermined location where sensor readings are taken.

6. The autonomous watercraft of claim 1, wherein the air sensor system comprises one or more air sensors selected from the group consisting of temperature sensors, barometric pressure sensors, and humidity sensors.

7. The autonomous watercraft of claim 1, comprising an air sensor for detecting toxic inorganic gases in the air surrounding the autonomous watercraft, wherein the air sensor detects, at least, the presence of hydrogen sulfide.

8. The autonomous watercraft of claim 1, wherein the deployment system comprises at least one cable coupled to a motor.

9. A system for analyzing a body of water used for hydraulic fracturing comprising an autonomous watercraft as described in claim 1 and a weather station positioned in the vicinity of the body of water, wherein the weather station measures one or more environmental conditions selected from the group consisting of: temperature, humidity, rainfall, wind speed wind direction, and solar radiation.

10. The system of claim 9, wherein the autonomous watercraft is operated to analyze the body of water when a change in the environmental conditions is detected by the weather station.

11. A method of analyzing a body of water used for hydraulic fracturing comprising:
    placing an autonomous watercraft, as described in claim 1, in the body of water, wherein the autonomous watercraft is programmed to:
        automatically deploy the water sensor system into the water at a predetermined depth and a predetermined location;
        automatically operate the air sensor system;
        automatically propel the autonomous watercraft along a predetermined route within the body of water, wherein the processor is operable to alter the predetermined route based on data obtained from the water sensor system; and
        automatically collect data from the water sensor system and/or the air sensor system and transmit the collected data to a location remote from the autonomous watercraft.

12. The method of claim 11, wherein the predetermined route is altered such that the autonomous watercraft is directed to chemically non-homogenous regions of the body of water.

* * * * *